United States Patent
Hall et al.

(10) Patent No.: US 10,080,859 B1
(45) Date of Patent: Sep. 25, 2018

(54) SHOULDER STRAP WITH RACEWAY FOR MEDICAL TUBING

(71) Applicants: Samuel Hall, Clever, MO (US); Michael T. Wise, Clever, MO (US)

(72) Inventors: Samuel Hall, Clever, MO (US); Michael T. Wise, Clever, MO (US)

(*) Notice: Subject to any disclaimer, the term of this patent is extended or adjusted under 35 U.S.C. 154(b) by 420 days.

(21) Appl. No.: 14/939,393

(22) Filed: Nov. 12, 2015

Related U.S. Application Data (60) Provisional application No. 62/078,939, filed on Nov. 12, 2014.

(51) Int. Cl.
| | |
|---|---|
| *A62B 7/00* | (2006.01) |
| *A62B 9/00* | (2006.01) |
| *A61M 16/08* | (2006.01) |
| *A61M 16/10* | (2006.01) |
| *A61M 16/06* | (2006.01) |

(52) U.S. Cl.
CPC .... *A61M 16/0875* (2013.01); *A61M 16/0672* (2014.02); *A61M 16/101* (2014.02); *A61M 2205/8206* (2013.01); *A61M 2209/088* (2013.01)

(58) Field of Classification Search
CPC .......... A61M 16/0875; A61M 16/0672; A61M 16/0683; A61M 2205/8206; A61M 2209/088
See application file for complete search history.

(56) References Cited

U.S. PATENT DOCUMENTS

| | | | | |
|---|---|---|---|---|
| 4,678,205 A | * | 7/1987 | Wold | B60R 22/00 280/808 |
| 4,685,456 A | * | 8/1987 | Smart | A61M 16/08 128/204.18 |
| 4,699,401 A | * | 10/1987 | Saenz | B60R 22/00 224/602 |
| 4,739,913 A | | 4/1988 | Moore | 224/215 |
| 4,786,080 A | * | 11/1988 | Jay | B60R 22/14 224/602 |
| 4,878,606 A | * | 11/1989 | Miller | A45F 3/14 224/610 |
| 5,188,267 A | | 2/1993 | Sargent et al. | 224/215 |
| 5,691,028 A | * | 11/1997 | Curtis | A41F 15/007 2/268 |
| 5,928,189 A | * | 7/1999 | Phillips | A61M 16/0677 604/65 |
| 6,003,744 A | * | 12/1999 | Culjak | A62B 25/00 128/205.22 |

(Continued)

*Primary Examiner* — Kristen Matter
(74) *Attorney, Agent, or Firm* — Jonathan A. Bay (57) ABSTRACT

A shoulder strap is provided with raceway provisions for medical tubing. The shoulder strap has opposite ends provided with male and female side-squeeze buckles. The raceway provisions are formed by an inner leaf and outer leaf which fold and fasten together for safely enclosing the medical tubing. The medical tubing extends between a nose piece and a connector end, wherein excess length of the medical tubing is usually coiled up in coils near the connector end. The shoulder strap further includes tubing traps which safely secure the coils. The tubing trap can be formed from snaps, buttons and/or hook-and-pile fastener material. The inner and outer leaves of the shoulder strap can be formed of any suitable material, such as that used in book bags except also provided with foam (cushion) cores.

15 Claims, 8 Drawing Sheets

(56) References Cited

U.S. PATENT DOCUMENTS

| | | | |
|---|---|---|---|
| 6,401,715 B1 | 6/2002 | Luthe | 128/205.28 |
| 6,409,271 B1 * | 6/2002 | Caramanis | B60R 22/00 |
| | | | 280/801.1 |
| 6,497,348 B2 | 12/2002 | Forsman et al. | 224/148.2 |
| 7,007,694 B2 | 3/2006 | Aylsworth et al. | 126/206.11 |
| 8,251,064 B2 | 8/2012 | Sanders | 128/205.22 |
| 8,302,830 B1 | 11/2012 | Jensen | 224/625 |
| 9,839,727 B2 * | 12/2017 | Anderson | A61M 1/0023 |
| 2005/0011520 A1 * | 1/2005 | Rowe | A62B 25/00 |
| | | | 128/205.22 |
| 2008/0223375 A1 | 9/2008 | Cortez et al. | 128/207.18 |
| 2009/0229603 A1 | 9/2009 | Grilliot | 128/202.19 |
| 2011/0197891 A1 | 8/2011 | Sanders | 128/205.22 |
| 2012/0310188 A1 * | 12/2012 | Croizat | A61M 1/0088 |
| | | | 604/319 |
| 2013/0275139 A1 * | 10/2013 | Coleman | A61M 16/0683 |
| | | | 704/275 |

* cited by examiner

SHOULDER STRAP WITH RACEWAY FOR MEDICAL TUBING

CROSS-REFERENCE TO PROVISIONAL APPLICATION(S)

This application claims the benefit of U.S. Provisional Application No. 62/078,939, filed Nov. 12, 2014. The foregoing patent disclosure is incorporated herein by this reference thereto.

BACKGROUND AND SUMMARY OF THE INVENTION

The invention relates to straps for housing or managing a cannula and, more particularly, to a shoulder strap that forms a raceway for flexible medical tubing.

Such medical tubing includes without limitation the oxygen supply tubing that is typically utilized by patients with chronic obstructive pulmonary disease (COPD) who carry portable oxygen concentrators (or generators) and/or portable oxygen bottles (or tanks) by means of a plain conventional shoulder strap.

In general public usage, the terms 'oxygen concentrators' and 'oxygen generators' are sometimes used interchangeably, but other times are used where 'concentrators' tend to refer to the smaller, portable and battery-powered units in contrast to 'generators,' which describes all other size plants. Oxygen 'bottles' (and 'tanks') are pressurized storage vessels, and are typically heavy and have to be re-charged/replaced when empty. With portable oxygen concentrators, keeping them operative is more a matter of keeping the battery charged.

A number of additional features and objects will be apparent in connection with the following discussion of preferred embodiments and examples.

BRIEF DESCRIPTION OF THE DRAWINGS

There are shown in the drawings certain exemplary embodiments of the invention as presently preferred. It should be understood that the invention is not limited to the embodiments disclosed as examples, and is capable of variation within the scope of the skills of a person having ordinary skill in the art to which the invention pertains. In the drawings.

FIG. 4 is an enlarged-scale perspective view of detail IV-IV in FIG. 2, except with the carrying case for the oxygen concentrator removed from view, and wherein this FIG. 4 shows a slightly different embodiment;

DETAILED DESCRIPTION OF THE PREFERRED EMBODIMENTS

Figure 1:
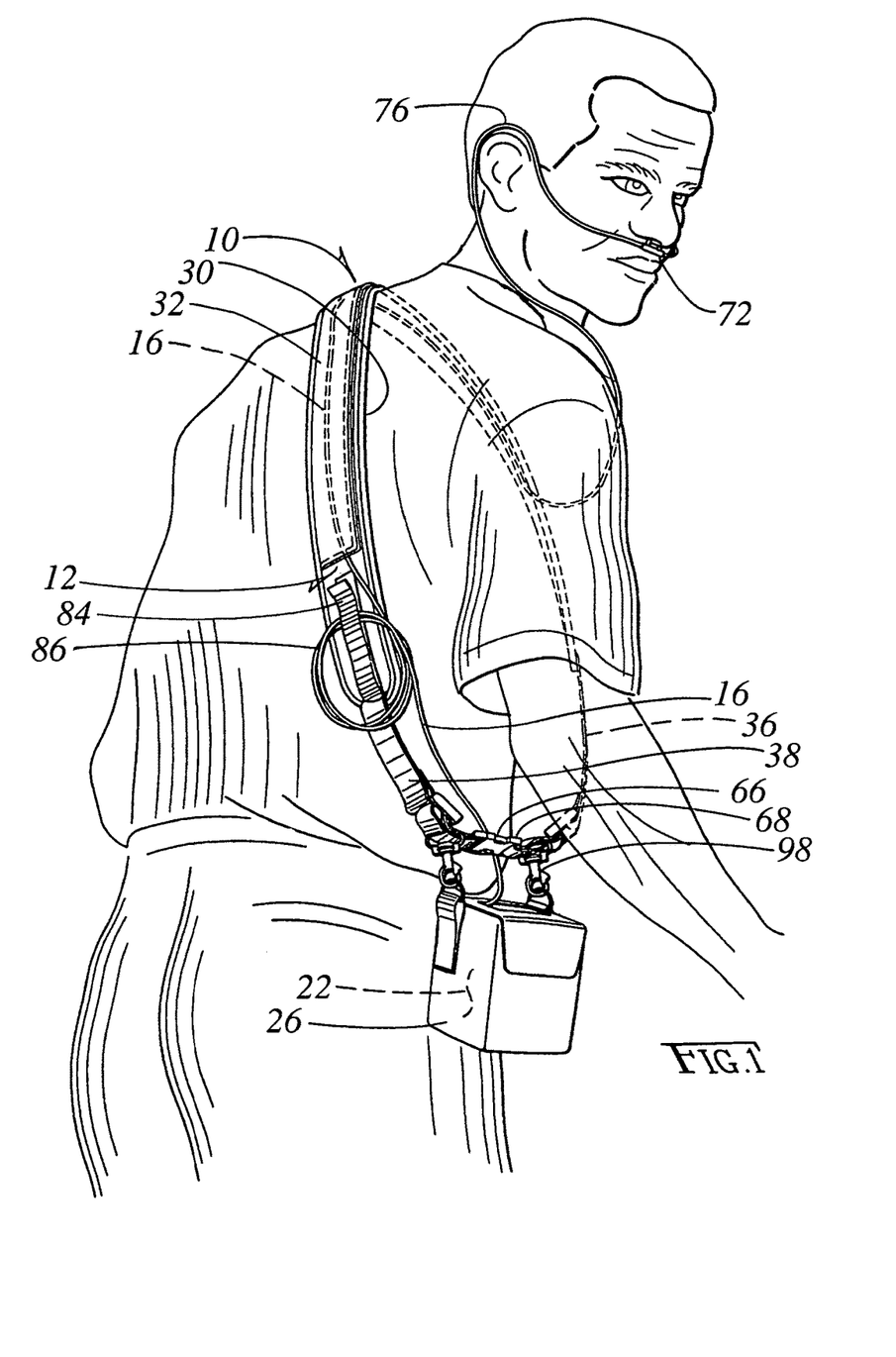
FIG. 1 is a perspective view a shoulder strap in accordance with the invention which is formed with a raceway for flexible medical tubing, and which shoulder strap is shown worn by a wearer carrying an oxygen concentrator to illustrate an example use environment.

FIGS. 1-8 show a shoulder strap 10 in accordance with the invention which is formed with a raceway 12 for channeling flexible medical tubing 16. FIG. 1 shows the shoulder strap 10 worn by a wearer carrying an oxygen concentrator 22 to illustrate an example use environment.

Such medical tubing 16 includes without limitation the oxygen supply tubing that is typically utilized by patients with chronic obstructive pulmonary disease (COPD) who carry portable oxygen concentrators (or generators) 22 and/or portable oxygen bottles (or tanks) 24 by means of a plain conventional shoulder strap (not shown).

Figure 2:
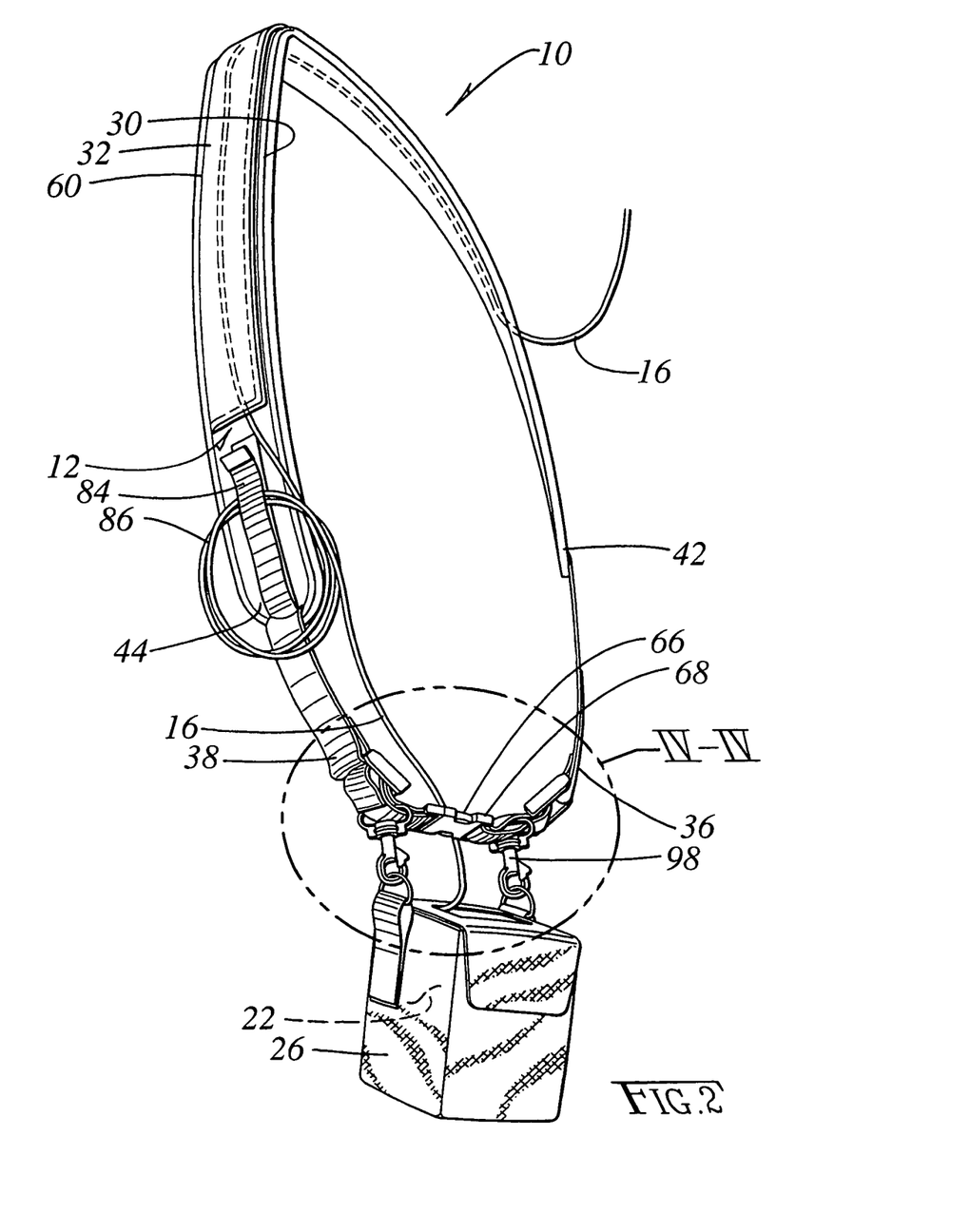
FIG. 2 is a perspective view comparable to FIG. 1 except on an enlarged scale and with the wearer removed from view.
Figure 3:
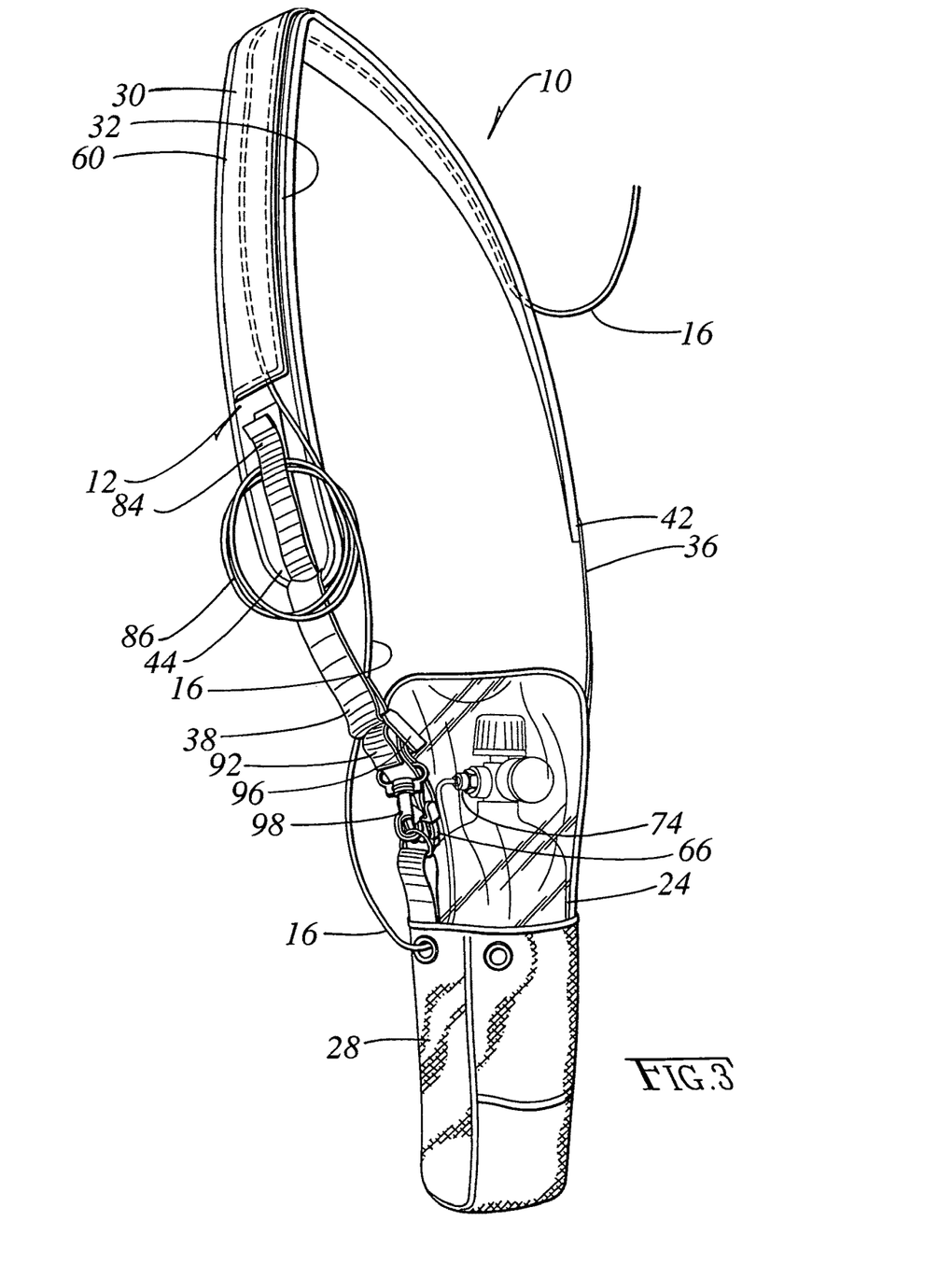
FIG. 3 is a perspective view comparable to FIG. 2 except showing a carry case for carrying an oxygen bottle rather than an oxygen concentrator as shown in FIG. 2.

FIGS. 1 and 2 show a carrying case 26 for an oxygen concentrator 22 suspended from the shoulder strap 10. FIG. 3 shows a carrying case 28 for an oxygen bottle 24 suspended from the shoulder strap 10.

The shoulder strap 10 is an elongated assembly comprising a central, shoulder-lapping raceway portion 30,32 flanked by a front-side fabric strap 36 portion and a counterpart back-side fabric strap 38 portion.

The central raceway portion 30,32 extends between a front end 42 and back end 44. Furthermore, the central raceway portion 30,32 comprises a folded structure comprising an inner leaf 30 and an outer leaf 32 which when compressed together form the raceway 12 (eg., interior channel) for medical tubing 16.

Figure 8:
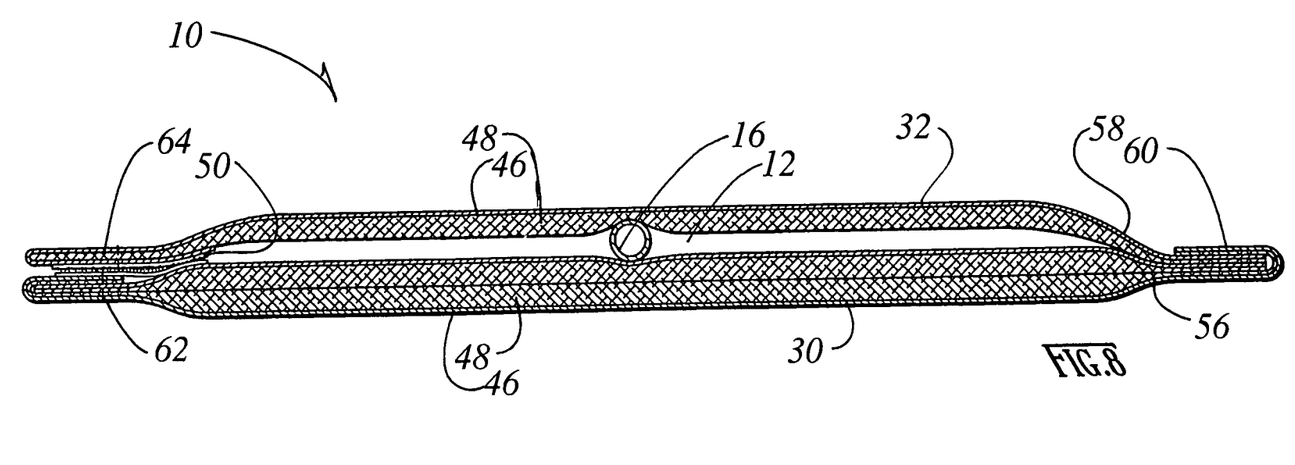
FIG. 8 is an enlarged scale section view taken along the line XIII-XIII in FIG. 7.

The inner leaf 30 is on the inside of the central raceway portion 30,32 and rests directly on the wearer's outer garments. The outer leaf 32, needless to say, is on the outside of the inner leaf 30. Both the inner leaf 30 and outer leaf 32 are constructed of soft flexible materials including without limitation (as FIG. 8 shows better) nylon-fabric sleeves 46 covering a foam core 48. The foam core 48, particularly for the inner leaf 30, provides cushioning for the wearer so that medical tubing 16 nested inside the raceway 12 is not felt by or else is not uncomfortable to the wearer. The foam core 48 for the outer leaf 32 is more a matter of hiding the medical tubing 16, so it doesn't bulge through the outer leaf 32 like a sinuous vein.

The inner and outer leaves 30 and 32 have facing interior sides which are provided with cooperative fasteners 50, such as and without limitation hook and pile fasteners 50. The inner leaf 30 is elongated and extends between a front-side end 42 and a back-side end 44. The outer leaf 32 is also elongated but is shorter than the inner leaf 30, and likewise extends between a front-side end 52 and a back-side end 54.

Given the foregoing, the shoulder strap 10 in accordance with the invention is provided with a raceway 12 through which medical tubing 16 can be extended by having some of the following characteristics.

The shoulder strap 10 comprises a first (eg., inner) elongated leaf 30 and a second (eg., outer) elongated leaf 32, each which extends longitudinally between opposite ends 42,44 and 52,54 and extends laterally between opposite edges 56,62 and 58,64. Preferably the second leaf 32 is shorter than the first leaf 30.

There is a buckle 66/68 (or buckle provisions 66 and 68) that is/are directly or indirectly connected to or connectable to the opposite ends 42,44 of the first leaf 30 (eg., the longer leaf 30).

The first and second leaves 30 and 32 are connected together by a seam 60 along one respective edge 56 and 58 of each of the first and second leaves 30 and 32. This seam 60 serves as a hinge between the two leaves 30 and 32. In view of the above, the second leaf 32 can be opened apart from and then shut closed with the first leaf 30 to define an interior raceway 12 with respect to the first leaf 30.

Moreover, there are fastening provisions 50 proximate the other edges 62 and 64 of the first and second leaf 30 and 32 for fastening shut the raceway 12. That way, medical tubing 16 can be inserted into the raceway 12 when the second leaf 32 is opened apart from the first leaf 30 and then safely secured therein by the fastening provisions 50.

The front-side end 52 and a back-side end 54 of the outer leaf 32 form the front-side outlet 52 and back-side inlet 54, respectively, of the raceway 12 for the medical tubing 16. It is an aspect of the invention that the shoulder strap 10 is scaled and proportioned so that the back-side inlet 54 is disposed somewhere above the wearer's rear hip on the wearer's same side on which the carrying case 26 or 28 is suspended. The shoulder strap 10 is furthermore scaled and proportioned so that the front-side outlet 52 is disposed somewhere around the wearer's collar bone on the wearer's opposite side from which the carrying case 26 or 28 is suspended.

Medical tubing 16 such as this and in accordance with the prior art is usually characterized by the following characteristics. The medical tubing 16 extends from a nosepiece 72 to a connector end 74 for connecting to an oxygen source (eg., perhaps an oxygen concentrator 22 or bottle 24 with optional flowmeters and the like).

Often times the tubing 16 emanates from the connector end 74 as a single conduit, but—before it reaches the nosepiece 72—it diverges at a wye to form a headset or lanyard loop 76 such that oxygen is supplied to the horizontal nosepiece 72 from both a left-side inlet port and a right-side inlet port.

The pair of leafs 30 and 32 can be undone at the fasteners 50, which will allow the outer leaf 32 to be folded apart from the inner leaf 30. The medical tubing 16 can be laid inside the open raceway 12, the user can fold the outer leaf 32 closed again, and re-fasten the fasteners 50. Thus a middle portion of the medical tubing 16 is secured inside the raceway 12. Also, this method of inserting the medical tubing 16 inside the raceway 12 does not have the user having to feed the medical tubing 16 into raceway 12 either by the connector end 74 or else the headset/lanyard loop 76.

The lengthier inner leaf 30 has a proximal end 78 of the back-side fabric strap 38 secured (eg., sewn) to its back-side end 44 and a counterpart proximal end 82 of the front-side fabric strap 36 secured (eg., sewn) to its front-side end 42.

At this same securement point between the proximal end 78 of the back-side fabric strap 38 and the back-side end 44 of the inner leaf 30, there is also secured thereto a tubing trap 84 for managing excess tubing length as shown in FIGS. 1 and 2. This excess-length tubing trap 84 is elongated along an axis that is parallel to the axis of the inner leaf 30. This excess-length tubing trap 84 may be constructed from, for example and without limitation, a pair of elongated strips of hook and pile material. The medical tubing 16 extends between a nosepiece 72 and a connector end 74, wherein excess length of the medical tubing 16 is coiled up in coils 86 near the connector end 74 and preferably secured by the excess-length tubing trap 84.

Figure 5:
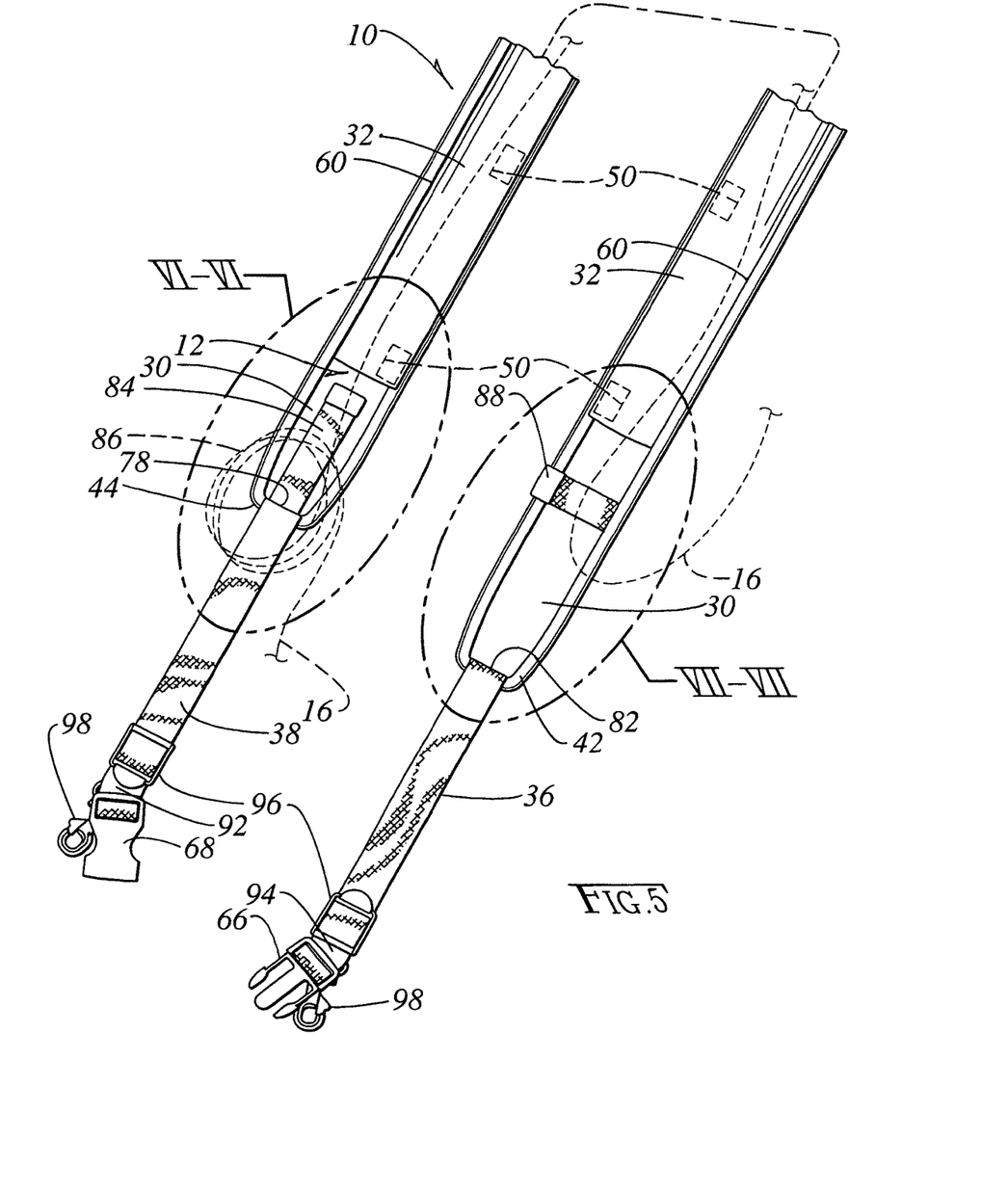
FIG. 5 is a plan view of the two ends of the shoulder strap in accordance with the invention, wherein middle portions are broken away.
Figure 6:
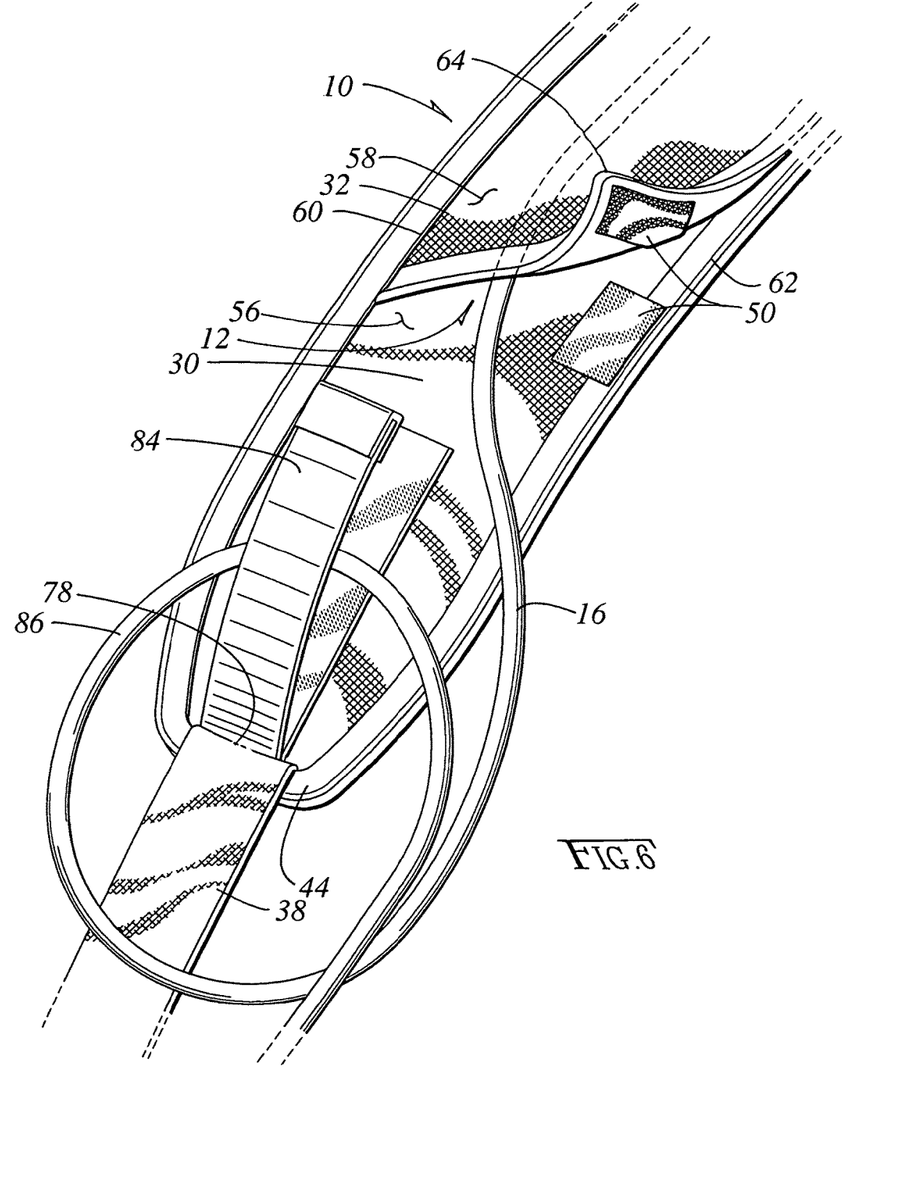
FIG. 6 is an enlarged-scale perspective view of detail VI-VI in FIG. 5.
Figure 7:
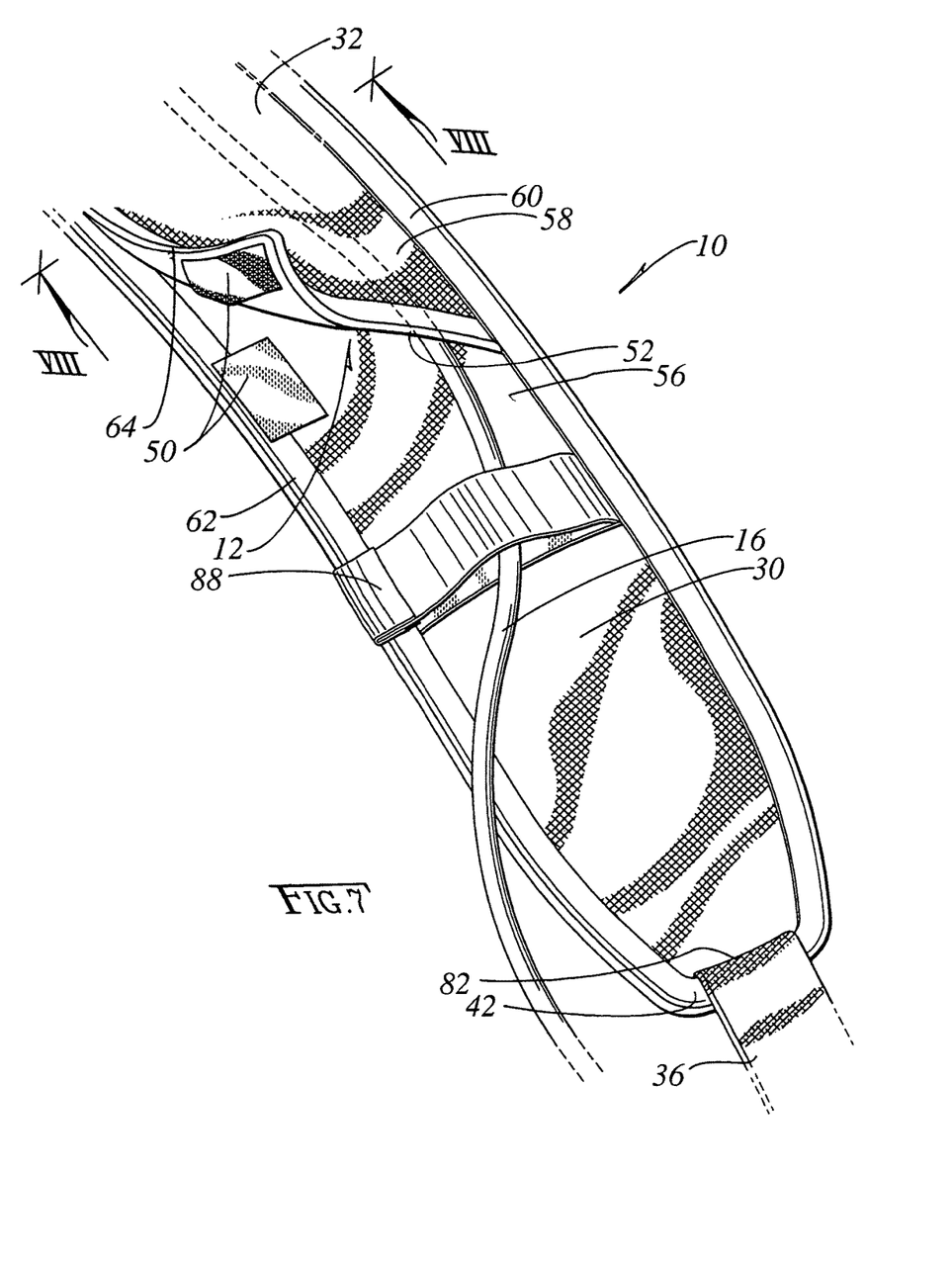
FIG. 7 is an enlarged-scale perspective view of detail VII-VII in FIG. 5.

Proximate the front-side, outlet end 52 of the raceway 12, the inner leaf 30 has secured to it another tubing trap 88, this one providing strain relief service for the medical tubing 16 as shown in FIG. 5, as the medical tubing extends away to the wye, headset/lanyard loop 76 and nosepiece 72 (these are not shown in FIG. 5). This strain-relief tubing trap 88 is elongated along an axis that is transverse to the axis of the inner leaf 30. This strain-relief tubing trap 88 may be constructed from, for example and without limitation, a pair of elongated strips of hook and pile material.

Figure 4:
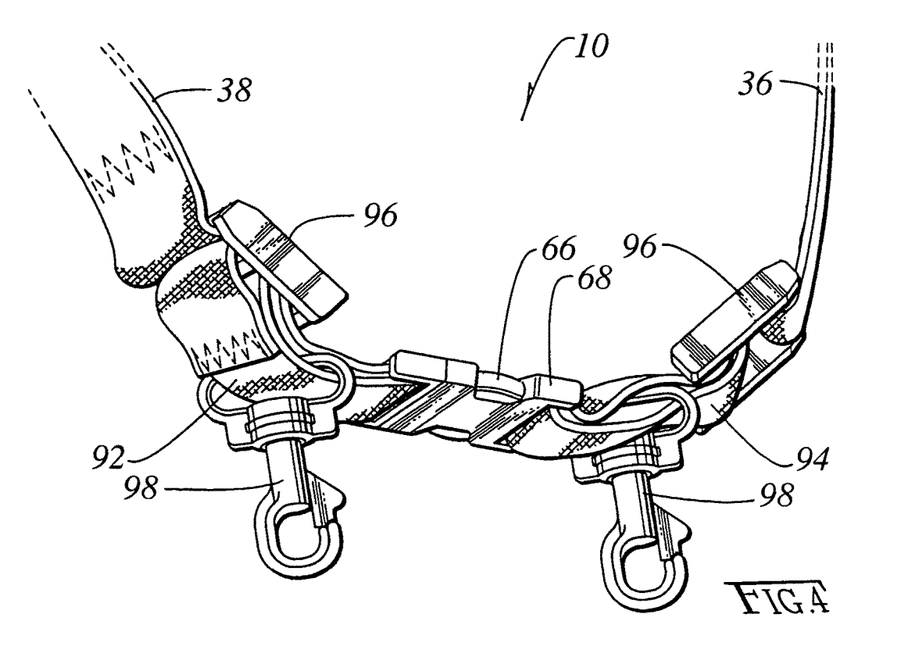

Each of the front-side fabric strap 36 and back-side fabric strap 38 extend from a respective proximal end 78 and 82, the securement of which to the ends 44 and 42 of the inner leaf 30 have already been described, to a respective distal end 92 and 94. As FIG. 4 shows better for one embodiment of the invention, each distal end 92 and 94 is first threaded through the two rectangular openings of a cinch slide 96, then through the rectangular opening of a bolt snap 98 (wherein the bolt snap 98 is simply left to dangle down), and onward through to the two rectangular openings of a male or female, respectively according to the circumstances, side-squeeze release buckle 66/68, to return to the cinch slide 96 and be looped around the center bar and wherein then the distal end 92,94 is sewn back on itself. However, FIG. 4 in fact differs in depicting how the distal ends 94 and 92 of the fabric straps 36 and 38 are preferably threaded. All the above-recited components are shown such as the cinch slides 96, bolt snaps 98, and male and female halves 66 and 68 of a side-squeeze release buckle 66/68. Despite that, the threading of the distal ends 92 and 94 through all of the above differs from how shown in contrast to how described above. The description above is preferred.

Preferably container cases 26 or 28 are suspended from the front and back bolt snaps as shown in FIGS. 1 through 3. The container cases 26 or 28 are removable from the shoulder strap 10 in accordance with the invention for the purposes of switching to a container case 28 or 26 for a different technology of oxygen source 24 or 22.

The cinch slides 96 on the respective front-side and back-side fabric straps 36 and 38 provide the shoulder strap 10 as a whole with adjustability for lengthening it or shortening it according to wearer comfort.

Given the foregoing, it is an aspect of the invention to better accommodate the extension of the medical tubing 16 between the oxygen source 22 or 24 and the nosepiece 72 by more safely running the medical tubing 16 through the raceway 12 of the shoulder strap 10 in accordance with the invention.

That is, the shoulder strap 10 in accordance with the invention protects the medical tubing 16 from being hooked on by things in the wearer's environment, including such typically non-threatening things as door knobs of doors.

The invention having been disclosed in connection with the foregoing variations and examples, additional variations will now be apparent to persons skilled in the art. The invention is not intended to be limited to the variations specifically mentioned, and accordingly reference should be made to the appended claims rather than the foregoing discussion of preferred examples, to assess the scope of the invention in which exclusive rights are claimed.

We claim:
1. A shoulder strap provided with a raceway through which medical tubing is extended, comprising:
   a first elongated leaf and a second elongated leaf, each extending longitudinally between opposite ends and laterally between opposite edges, wherein the second leaf is shorter than the first leaf;
   a buckle directly or indirectly connected to or connectable to the opposite ends of the first leaf;

the first and second leafs being connected by a seam along one respective edge of each of the first and second leaf, whereby the second leaf can be opened apart from and then closed shut with the first leaf to define an interior raceway with respect to the first leaf; and fastening provisions proximate each of the other edge of the first and second leaf for fastening shut the raceway, whereby medical tubing can be inserted into the raceway when the second leaf is opened apart from the first leaf and then safely secured therein by the fastening provisions.

2. The shoulder strap of claim 1, further comprising:

a portable, battery-powered oxygen concentrator;

flexible medical tubing, comprising oxygen supply tubing utilized by patients who carry portable, battery-powered oxygen concentrators;

a carrying case for the oxygen concentrator; and snap provisions directly or indirectly connected to or connectable to the opposite ends of the first leaf, said snap provisions removably carrying the carrying case for the oxygen concentrator;

whereby the shoulder strap is wearable by a wearer thereof such that the oxygen concentrator is hung along one hip thereof.

3. The shoulder strap of claim 2, further comprising:

said flexible medical tubing is elongate between one end, comprising a permanently formed nosepiece, and, another end comprising a permanently attached connector for connecting to the oxygen concentrator.

4. The shoulder strap of claim 3, wherein:

said one end of the flexible medical tubing further comprises a single conduit that diverges at a wye to form a headset or lanyard loop, with the nosepiece formed therein, whereby oxygen is supplied to the horizontal nosepiece from both a left-side inlet port and a right-side inlet port.

5. The shoulder strap of claim 1, further comprising:

a portable, pressurized oxygen bottle;

flexible medical tubing, comprising oxygen supply tubing utilized by patients who carry portable, pressurized oxygen bottles;

a carrying case for the portable, pressurized oxygen bottle; and snap provisions directly or indirectly connected to or connectable to the opposite ends of the first leaf, said snap provisions removably carrying the carrying case for the portable, pressurized oxygen bottle;

whereby the shoulder strap is wearable by a wearer thereof such that the portable, pressurized oxygen bottle is hung along one hip thereof.

6. The shoulder strap of claim 5, further comprising:

said flexible medical tubing is elongate between one end, comprising a permanently formed nosepiece, and, another end comprising a permanently attached connector for connecting to the portable, pressurized oxygen bottle.

7. The shoulder strap of claim 6, wherein:

said one end of the flexible medical tubing further comprises a single conduit that diverges at a wye to form a headset or lanyard loop, with the nosepiece formed therein, whereby oxygen is supplied to the horizontal nosepiece from both a left-side inlet port and a right-side inlet port.

8. A shoulder strap provided with a raceway through which medical tubing is extended, comprising:

an inner elongated leaf and an outer elongated leaf, each extending longitudinally between a respective front-side end and back-side end, and laterally between opposite edges, whereby the shoulder strap is worn by a wearer thereof over-slung across one shoulder and with the front-side and back-side ends of the inner leaf converging alongside a hip of the wearer on the opposite side of the over-slung shoulder;

the inner and outer leafs being connected by a seam along one respective edge of each of the inner and outer leaf, whereby the outer leaf can be unfolded apart from and then folded back shut with the inner leaf to define an interior raceway with respect to the inner leaf;

a portable oxygen source;

flexible medical tubing, comprising oxygen supply tubing utilized by patients who carry such portable oxygen sources;

a carrying case for the portable oxygen source; and a pair of snap provisions directly or indirectly connected to or connectable to one front-side end of either the inner or outer leaf and one back-side end of either the inner or outer leaf, said snap provisions removably carrying the carrying case for the portable oxygen source;

whereby the outer leaf can be unfolded apart from the inner leaf while said shoulder strap is being worn by the wearer, so as to allow opportunity to insert said flexible medical tubing into the raceway while the outer leaf is unfolded apart from the inner leaf, and thereafter allow the outer leaf to fold back shut with the inner leaf thereby closing said flexible medical tubing in the raceway;

said shoulder strap further comprising:

a front-side strap portion, and, a back-side strap portion;

wherein the front-side end of the inner leaf is connected to the front-side strap portion;

the back-side end of the inner leaf is connected to the back-side strap portion; and one of the pair of snap provisions is connected to the front-side strap portion as the other of the pair of snap provisions is connected to the back-side strap portion.

9. The shoulder strap of claim 8, further comprising:

fastening provisions proximate each of the other edge of the inner and outer leaf for fastening shut the raceway.

10. The shoulder strap of claim 9, wherein:

both leafs are constructed of soft flexible materials including a foam core; and said fastening provisions comprise hook and pile fasteners.

11. The shoulder strap of claim 8, further comprising:

a strap shortening provision provided on at least one of the front-side strap portion or back-side strap portion, whereby said shoulder strap overall is adjustable for wearer size and comfort.

12. The shoulder strap of claim 8, further comprising:

an excess-length tubing trap;

wherein said back-side strap portion extends between a distal end and a proximal end connected to the back-side end of the inner leaf;

said excess-length tubing trap is connected to one or the other of the back-side strap portion or the inner leaf proximate the proximal end or the back-side end of each respectively; and said excess-length tubing trap configured to secure excess tubing length in loose coils behind the back of the wearer.

13. The shoulder strap of claim 12, wherein:

said excess-length tubing trap comprises an elongated strap that is elongate along a longitudinal axis that is parallel to a counterpart longitudinal axis for the inner leaf; and said excess-length tubing trap comprising spaced hook and pile fasteners on one face whereby said excess-length tubing strap can be folded to mate the hook and pile fasteners provisions.

14. The shoulder strap of claim 8, further comprising:

a strain-relief tubing trap;

wherein said flexible medical tubing is elongate between one end, comprising a permanently formed nosepiece, and, another end terminating in an attached connector for connecting to the portable oxygen source;

said front-side strap portion extends between a distal end, and, a proximal end connected to the front-side end of the inner leaf;

said strain-relief tubing trap is connected to one or the other of the front-side strap portion or the inner leaf proximate the proximal end or the front-side end of each respectively; and said strain-relief tubing trap securing the tubing proximate the nose-piece such that tension on the tubing towards the connector end is relieved at the strain-relief tubing trap whereby the nose-piece is not ripped off the wearer.

15. The shoulder strap of claim 14, wherein:

said strain-relief tubing trap comprises an elongated strap that is elongate along a longitudinal axis that is parallel to a counterpart longitudinal axis for the inner leaf; and said strain-relief tubing trap comprising spaced hook and pile fasteners on one face whereby said strain-relief tubing strap can be folded to mate the hook and pile fasteners provisions.

\* \* \* \* \*